United States Patent
Bradbury et al.

(10) Patent No.: US 9,220,274 B2
(45) Date of Patent: Dec. 29, 2015

(54) METHOD TO REMEDIATE A MOLLUSK INFESTATION

(71) Applicant: WISEARTH IP, INC., Plano, TX (US)

(72) Inventors: Rod S. Bradbury, Saanichton (CA); Robert Michael Lockerd, Sr., Plano, TX (US); Deborah A. Chadbourne, Bethlehem, PA (US)

(73) Assignee: WISEARTH IP, INC., Plano, TX (US)

( * ) Notice: Subject to any disclaimer, the term of this patent is extended or adjusted under 35 U.S.C. 154(b) by 0 days.

(21) Appl. No.: 14/244,609

(22) Filed: Apr. 3, 2014

(65) Prior Publication Data

US 2014/0220092 A1 Aug. 7, 2014

Related U.S. Application Data

(63) Continuation of application No. 13/617,410, filed on Sep. 14, 2012, now Pat. No. 8,771,762.

(60) Provisional application No. 61/534,486, filed on Sep. 14, 2011.

(51) Int. Cl.
| | |
|---|---|
| *A61K 36/00* | (2006.01) |
| *A01N 65/08* | (2009.01) |
| *A61K 36/185* | (2006.01) |
| *C02F 1/68* | (2006.01) |
| *A01N 65/00* | (2009.01) |
| *B63J 4/00* | (2006.01) |
| *C02F 1/50* | (2006.01) |
| *B08B 9/027* | (2006.01) |
| *C02F 103/00* | (2006.01) |

(52) U.S. Cl.
CPC .............. *A01N 65/08* (2013.01); *A01N 65/00* (2013.01); *A61K 36/185* (2013.01); *B08B 9/027* (2013.01); *B63J 4/00* (2013.01); *C02F 1/505* (2013.01); *C02F 1/688* (2013.01); *C02F 2103/008* (2013.01)

(58) Field of Classification Search
None
See application file for complete search history.

(56) References Cited

U.S. PATENT DOCUMENTS

| | | | |
|---|---|---|---|
| 3,732,202 | A | 5/1973 | Jewers et al. |
| 4,154,818 | A | 5/1979 | Kanada et al. |
| 5,252,330 | A | 10/1993 | Lee et al. |
| 5,334,386 | A | 8/1994 | Lee et al. |
| 2006/0182776 | A1 | 8/2006 | Voris et al. |
| 2007/0196517 | A1 | 8/2007 | San Martin |
| 2009/0111694 | A1 | 4/2009 | Dituro |

FOREIGN PATENT DOCUMENTS

| | | | |
|---|---|---|---|
| CA | 2034414 A1 | | 4/1992 |
| JP | 2002154907 A | * | 5/2002 |
| WO | 9308686 A1 | | 5/1993 |
| WO | 0056150 A1 | | 9/2000 |

OTHER PUBLICATIONS

Lemma, Endod is lethal to zebra mussels and inhibits their attachment, Journal of Shellfish Research, (1991) vol. 10, No. 2, pp. 361-366.*
Singapore Search Report and Written Opinion for Application No. 11201402886Q mailed Mar. 31, 2015, 9 pages.
Lemma, "Laboratory and Field Evaluation of the Molluscicidal Properties of Phytolacca dodecandra", Bull. Wld Hlth Org. 1970, 42, pp. 597-612.
Lemma, et al., "Studies on the Molluscicidal Properties of Endod (Phytolacca Dodecandra): I. Increased Potency With Butanol Extraction", The Journal of Parasitology, vol. 58, No. 1, Feb. 1972, pp. 104-107.
Eguale, et al., "Molluscicidal Effects of Endod (Phytolacca Dodecandra) on Fasciola Transmitting Snails" Ethiop. J. Sci. 25(2), 2002, pp. 275-284.

* cited by examiner

*Primary Examiner* — Qiuwen Mi
(74) *Attorney, Agent, or Firm* — David W. Carstens; Shaukat A. Karjeker; Carstens & Cahoon, LLP

(57) ABSTRACT

A device for treating pests and method for using the same. The device comprises an effective amount of endod. The device can be placed in a body of water wherein the endod treats the pests. Additionally the device can be placed in a pipe whereby a combination of the endod and the mechanical force of the water removes the pests in the pipe.

18 Claims, 1 Drawing Sheet

METHOD TO REMEDIATE A MOLLUSK INFESTATION

CROSS-REFERENCE TO RELATED APPLICATION

This application is a continuation of U.S. Ser. No. 13/617,410 filed Sep. 14, 2012 which is in turn a continuation-in-part of U.S. Provisional Patent Application Ser. No. 61/534,486, entitled "Method and Apparatus for Treating Pests," filed Sep. 14, 2011, the technical disclosures of which are hereby incorporated herein by reference.

BACKGROUND OF THE INVENTION

1. Technical Field

The present invention relates to a method and apparatus for controlling water pests.

2. Description of Related Art

Mussels and other such water pests infest waterways and clog intake pipes. One such example is the Zebra mussel, *Dreissena polymorphs*. These mussels attach and cluster atop virtually any solid surface. This is problematic when the surface is a water intake pipe as the mussels restrict flow through the pipe. Further mussels undesirably attach to ships' ballasts. Finally, these and other pests often carry dangerous and undesirable diseases, including water borne diseases, which are harmful to humans or other wildlife. Consequently, there is a need to be able to kill or remove the mussels and other such pests.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

DETAILED DESCRIPTION

Several embodiments of Applicants' invention will now be described with reference to the drawings. Unless otherwise noted, like elements will be identified by identical numbers throughout all figures. The invention illustratively disclosed herein suitably may be practiced in the absence of any element which is not specifically disclosed herein.

It has been discovered that *Phytolacca dodecandra*, generally known as Endod or African Soapberry, is useful in the killing of mussels and other such water pests. One example of such pests is the Zebra mussel. Pests include mussels, snails, mollusks, and other such life forms which are to be controlled. These pests often carry many diseases which can be spread to humans and domesticated animals. For example schistosomiasis is spread via snails. This is very common in rice paddies throughout Asia. Consequently, by controlling snails, for example, the spread of schistosomiasis can be decreased.

Endod is degradable which makes it suitable for use in waterways. It is believed that the effective ingredient in endod is saponin. Endod has been found safe for humans and domesticated animals. Thus, endod can be applied in common waterways with minimal, if any, unintended environmental impact.

Successful application of endod results in either killing the pest or rendering them incapable of latching onto surfaces. An application of endod which results in either the killing of pests, or rendering them incapable of latching onto surfaces is referred to as an effective application. The concentration of endod as well as the length of application can be adjusted during the application to reach an effective application. It can be appreciated that in some embodiments an effective application can comprise a lower concentration (ppm) along with a longer application (hours).

Endod can be applied in a variety of different ways. In one embodiment the endod berries are ground to form a powder. The powder can then be suspended in a liquid medium, such as water. The amount of endod in the solution can be adjusted, but it has been found that an effective concentration of between 5 ppm and about 20 ppm has been sufficient to either kill pests or render them incapable of latching onto surfaces.

Figure 1:
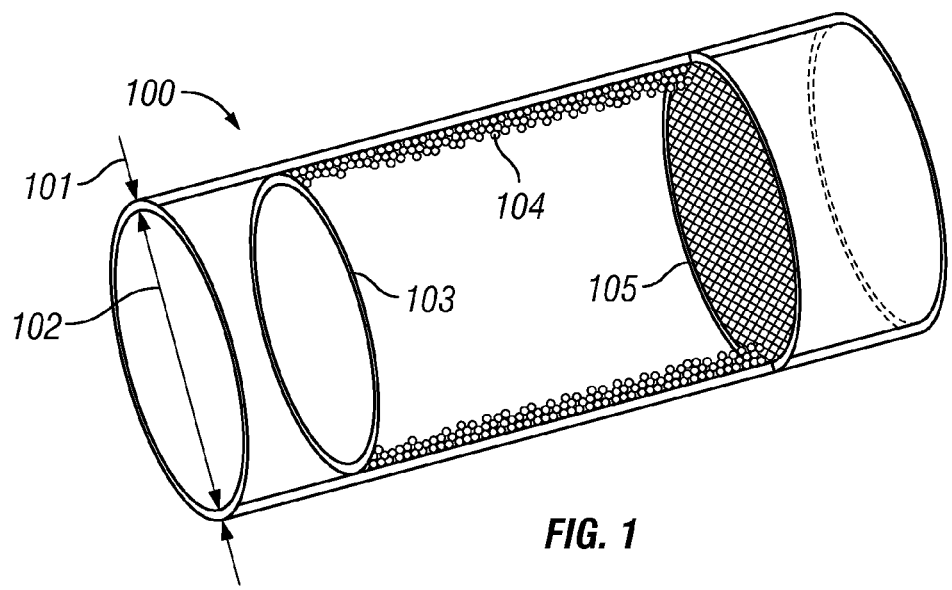
FIG. 1 is a perspective view of one embodiment of an endod device in a disk shape.

FIG. 1 is a perspective view of one embodiment of an endod device in a disk shape. FIG. 1 shows a pipe 100. The pipe 100 can be an intake pipe, an outlet pipe, virtually any pipe through which water flows. As illustrated the pipe 100 has an outer diameter 101, and an inner diameter 102.

FIG. 1 also shows an endod device 103. An endod device 103 is a device which comprises endod. The endod can be contained within the device 103 or the endod can be applied to the surface of the endod device 103. In one embodiment, the endod is applied to the device 103 via a binder. A binder is any substance which holds endod within and/or onto the device 103. The endod can be dissolved in the binder, or the endod can be applied to the surface of the binder. As will be described below, in one embodiment the binder is water soluble.

As depicted the endod device 103 comprises a disk, although the device 103 can comprise a variety of shapes. In one embodiment the device 103 has an outer diameter which is slightly less than the inner diameter 102 of the pipe 100. Slightly less refers to a first value which is between about 80% and about 100% of a second value. In one embodiment the device 103 has an outer diameter which is between about 90% and about 100% of the inner diameter 102 of the pipe 100.

As depicted the device 103 is a disk which has a central opening. In other embodiments the disk comprises two or more openings. In still other embodiments the device 103 does not comprise a central opening but instead is water permeable. In such an embodiment water flows through the device 103. In one embodiment the shape of the device 103 is substantially similar to the cross-section of the pipe 100. In other embodiments the device 103 comprises the shape of a cube, ball, or other solid surface. The device 103 can comprise virtually any shape.

As noted, in one embodiment the device 103 comprises endod. In one embodiment the endod device 103 comprises a slow release endod device. As used herein, a slow release endod device is a device which is still releasing endod after 2 hours. In one embodiment the slow release endod is still releasing endod after 8 hours. The time release properties of the endod on the device 103 can be adjusted for a variety of factors including the size of the pipe, the flow rate through the pipe, the length of the pipe, etc. It can be appreciated that if all of the endod was simply released at a single point, the endod would disperse through and with the flowing fluid. As such, the residence time of the endod within the pipe and around the pests would be minimal. However, a slow release allows some endod to be released over time which increases the time in which the pests are exposed to endod, referred to herein as the exposure time.

It has been discovered that some mussels and other such pests can sense chlorine and other chemicals in the water. When this happens, the pests do not circulate or otherwise take-in air and/or water for a period of between 1 and 8 hours. Accordingly, in one embodiment the duration of the application of the endod is greater than 8 hours. This ensures the exposure time will be greater than the time that the pests do not circulate air/water. Consequently, the pest will be exposed to endod. As such, in one embodiment the slow release properties of the disk allow the endod to be released for a period greater than 8 hours.

The time release properties of the endod and the device 103 can be achieved in a variety of ways. In one embodiment the endod is encapsulated in the device 103 via a binder. As noted, in one embodiment the binder comprises a water soluble substance. Thus, as the water soluble substance dissolves over time, the endod which was encapsulated or otherwise sealed by the water soluble substance is released. The water soluble substance can comprise any substance which slowly dissolves in water and which is non-reactive to the endod. Examples of such a water soluble substance includes but is not limited to some salts and sugars.

Figure 2:
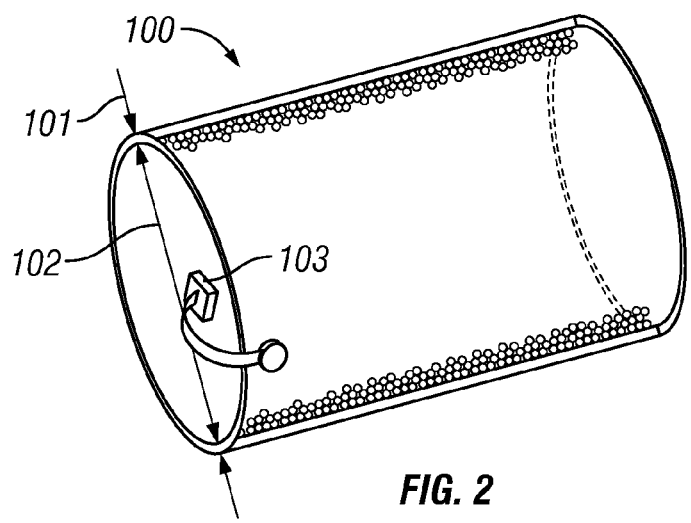
FIG. 2 is a perspective view of an endod device in one embodiment.

In one embodiment the device 103 is a permanent feature secured temporarily to a location upstream of the pests which are to be removed. For example, the device 103 can be located near the intake of the pipe 100. FIG. 2 illustrates a perspective view of an endod device in one embodiment. The device 103 can be secured via any device known in the art including welding, screwing, bolting, etc. Thus, water flows around and/or through the device 103 and distributes the endod to the pests 104.

Referring back to FIG. 1 it can be seen that the device 103 comprises a disk shape. As noted, in one embodiment the outer diameter of the device 103 is slightly less than the inner diameter of the pipe 100. In one embodiment the device 103 operates as previously described by releasing endod over time. Thus, the pests 104 of this embodiment are removed via a chemical means. However, in one embodiment the device 103 further provides a mechanical force to remove the pests. As seen in FIG. 1, water applies a force against the device 103 in an attempt to push the device 103 downstream. As the device 103 is forced downstream it slowly releases endod. Simultaneously, while advancing downstream the device 103 brushes against the inner diameter 102 of the pipe 100. While advancing downstream, however, the device 103 is stopped by the presence of mussels 104 which have yet to release. Put differently, the device 103 cannot advance downstream because pests 104 block the device's 103 further movement. As such, the force of the water pressed against the downstream end of the device 103 which applies a force against the pests 104. The obstructing pests 104 become weak due in part to the presence of the endod as well as the pressure of the device 103. Thus, the obstructing pests 104 eventually lose their grip and fall. The device 103 is then advanced further downstream where it may or may not abut against additional obstructing pests 104.

As noted, in one embodiment the endod device 103 maintains its shape as it advances through the pipe 100. As such, in one embodiment the endod device 103 comprises sufficient rigidity to retain its shape. In such embodiments, this rigidity prevents the endod device 103 from contorting. Accordingly, the endod device 103 maintains its shape and thus advances along the inside diameter of the pipe 100. Without sufficient rigidity, the endod device 103 could bend and flow through the pipe 100 without encountering any obstructing pests 104.

As described there are several methods of treating pests utilizing an endod device. In one embodiment an endod device is first obtained. Thereafter, the endod device is placed in a pipe. In one embodiment the device is secured within the pipe. In other embodiments the endod device is advanced downstream through the pipe.

This method offers several unexpected benefits. First, this method allows the combination of mechanical and chemical means to remove the pests. Further, in one embodiment because the released endod is in close proximity with the obstructing mussel, the obstructing mussel receives a high concentration blast of endod. This is because the endod has not yet had an opportunity to diffuse within the flowing water. Thus, the obstructing pests receive a concentrated blast of endod as well as an applied force of the device 103. The combined forces ensure the pests release their grip.

Another benefit is that, in some embodiments, when the device 103 reaches any downstream location, the operator is ensured that the pipe surfaces upstream of the device 103 have been successfully cleaned. As an example, in FIG. 1 the pipe comprises a removable filter 105. A filter prevents larger items from passing downstream of the filter. For example, if FIG. 1 shows the intake to a pump it may be desirable to minimize the passage of any large items to the pump. A removable filter 105 helps trap items of a specified size from flowing downstream of the filter. Any filter 105 known in the art can be used. As noted above, if the device 103 is stopped at the filter 105, then the operator knows that the pipe 100 upstream of the filter 105 has been successfully cleaned. The filter 105 can also act to capture released pests. It should be noted that in some embodiments the entire endod device 103 is water soluble.

Figure 3:
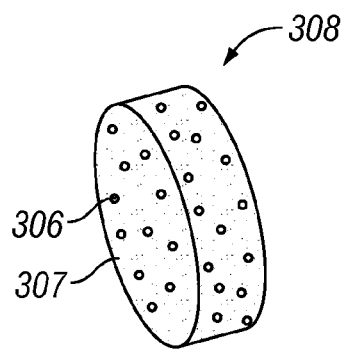
FIG. 3 is a perspective view of an endod tablet in one embodiment.

FIG. 3 is a perspective of an endod tablet in one embodiment. In this embodiment the tablet 308 comprises endod 306 as well as a water soluble binder 307. In operation the tablet 308 is dropped into a body of water comprising pests. In one embodiment the tablet 308 is a time release tablet which releases endod over time. In one embodiment the tablet 308 is still releasing endod after 8 hours. The water soluble substance 307 can comprise any water soluble substance previously described. The amount of endod 306 per tablet can be adjusted for a variety of factors.

In operation at least one tablet 308 is inserted within a body of water comprising pests. The tablet 308 releases the endod 306 which subsequently kills the pests or renders them incapable of latching onto solid surfaces. In one embodiment the first step is determining the amount of endod required for an effective application. In one embodiment the first step comprises determining the approximate volume of water to be treated. Thereafter, the proper amount of tablets 308 is inserted into the water.

As noted, there are several unexpected results. First, removing undesirable pests from solid surfaces resulted in increased flow though pipes, better functioning ballasts, and cleaner solid surfaces. Additionally, killing disease carrying pests prevents the spreading of many diseases. Finally, because endod is safe for the environment and humans, any unintended environmental concerns are minimized.

In still another embodiment pipes and other items, such as a ship's ballast, are pre-treated with endod. For example, a pipe can be coated with a slow release coating which comprises endod. In one embodiment the slow release coating slowly releases endod for a period of many months. In such embodiments the pre-coated pipes would prevent the accumulation of pests. This method can be supplemented with the other methods and devices discussed herein.

While the invention has been particularly shown and described with reference to a preferred embodiment, it will be understood by those skilled in the art that various changes in form and detail may be made therein without departing from the spirit and scope of the invention.

What is claimed is:

1. A method of treating water to remediate a mollusk infestation, the method comprising the steps of:
    a. selecting an amount of a formulation comprising an extract from Phytolacca dodecandra and a binder;
    b. depositing the selected amount of the formulation in the water to be remediated for a mollusk infestation;
    c. allowing the extract to disperse in the water to cause an effective lethal concentration of the extract in the water; and
    d. maintaining said effective lethal concentration of extract in the water for an exposure time comprising of from about 1 to about 8 hours to remediate the mollusk infestation.

2. The method of claim 1, wherein step (c) further comprises providing an effective extract concentration of between about 5 ppm and about 20 ppm.

3. The method of claim 1, wherein step (a) comprises selecting a formulation having a time-controlled release.

4. The method of claim 1 wherein step (a) comprises selecting a formulation that is a powder.

5. The method of claim 1 wherein step (a) comprises selecting a formulation in the form of a tablet.

6. The method of claim 1 wherein step (a) comprises selecting a formulation in the form of a disc.

7. The method of claim 1 comprising remediating an infestation of snails.

8. The method of claim 1, comprising remediating an infestation of zebra mussels.

9. A method of treating water to diminish a snail infestation, the method comprising the steps of:
    a. calculating an amount of Phytolacca dodecandra extract to achieve a concentration of extract in the water that is lethal to and/or inhibiting of reproduction by the snails;
    b. selecting a quantity of a formulation comprising the calculated amount of the extract and a binder;
    c. depositing the selected quantity of the formulation in the water;
    d. allowing the extract to disperse in the water to cause a concentration of the extract in the water to rise to a concentration lethal to and/or inhibiting of reproduction by the snails; and
    e. maintaining the extract the concentration in the water that is lethal to and/or inhibiting of reproduction by the snails for an exposure time to diminish the snail infestation.

10. The method of claim 9, wherein step (e) comprises maintaining the concentration of the extract between about 5 ppm and about 20 ppm for an exposure time of about 1 to about 8 hours in the water.

11. The method of claim 9, wherein step (e) comprises maintaining the concentration of the extract between about 5 ppm and about 20 ppm for an exposure time of more than 8 hours in the water.

12. The method of claim 9 wherein step (b) comprises selecting a formulation that is a powder.

13. The method of claim 9, wherein step (b) comprises selecting a formulation that has a time-controlled-release.

14. The method of claim 9 wherein step (b) comprises selecting a formulation in a form of a tablet.

15. The method of claim 9 wherein step (b) comprises selecting a formulation in a form of a disc.

16. A method of treating water to remediate a mollusk infestation, the method comprising the steps of
    a. selecting an amount of a formulation comprising an extract from Phytolacca dodecandra and a binder;
    b. depositing the selected amount of the formulation in the water;
    c. allowing the extract to disperse in the water to cause an effective lethal concentration of from about 5 ppm to about 20 ppm in the body of water; and
    d. maintaining said effective lethal concentration of extract for an exposure time of more than about 8 hours to remediate the mollusk infestation in the water.

17. The method of claim 16 comprising remediating an infestation of snails.

18. The method of claim 16 comprising remediating an infestation of zebra mussels.

* * * * *